United States Patent
Youman

(10) Patent No.: US 11,918,743 B1
(45) Date of Patent: Mar. 5, 2024

(54) OXYGEN MASK

(71) Applicant: Rodney Youman, New York, NY (US)

(72) Inventor: Rodney Youman, New York, NY (US)

(*) Notice: Subject to any disclaimer, the term of this patent is extended or adjusted under 35 U.S.C. 154(b) by 396 days.

(21) Appl. No.: 17/120,393

(22) Filed: Dec. 14, 2020

(51) Int. Cl.
*A61M 16/08* (2006.01)
*A61M 16/06* (2006.01)
*A61M 16/20* (2006.01)
*A62B 18/02* (2006.01)
*A62B 18/08* (2006.01)
*A62B 23/02* (2006.01)

(52) U.S. Cl.
CPC .... *A61M 16/0816* (2013.01); *A61M 16/0672* (2014.02); *A61M 16/0683* (2013.01); *A62B 18/025* (2013.01); *A62B 18/08* (2013.01); *A62B 23/025* (2013.01); *A61M 16/201* (2014.02)

(58) Field of Classification Search
CPC .......... A61M 16/0672; A61M 16/0816; A61M 16/0683; A61M 16/201; A61M 16/0666; A62B 18/02; A62B 18/025; A62B 18/04; A62B 18/08; A62B 23/025; A62B 7/12; A62B 18/003; A62B 18/006
See application file for complete search history.

(56) References Cited

U.S. PATENT DOCUMENTS

| 2,675,803 | A | 4/1954 | Kaslow |
| 4,201,205 | A | 5/1980 | Bartholomew |
| 4,233,972 | A | 11/1980 | Hauff et al. |
| 5,005,571 | A | 4/1991 | Dietz |
| 5,233,978 | A | 8/1993 | Callaway |
| 6,386,198 | B1 | 5/2002 | Rugless |
| 6,691,702 | B2 | 2/2004 | Appel et al. |
| 9,675,774 | B2 | 6/2017 | Cipollone et al. |
| 10,335,569 | B2 | 7/2019 | Beard et al. |
| 2009/0084385 | A1 | 4/2009 | Lang |
| 2018/0085544 | A1* | 3/2018 | Holyoake ........... A61M 16/202 |
| 2022/0072340 | A1* | 3/2022 | Nitta ................. A62B 7/10 |

FOREIGN PATENT DOCUMENTS

| CN | 204121559 U | 1/2015 |
| CN | 105194777 B | 12/2015 |
| CN | 108883320 A | 11/2018 |
| WO | WO-2014031671 A1 * | 2/2014 ............. A42B 3/286 |

* cited by examiner

*Primary Examiner* — Kendra D Carter
*Assistant Examiner* — Mautin I Ashimiu
(74) *Attorney, Agent, or Firm* — Gerben Perrott, PLLC; Benjamin M. Hanrahan

(57) ABSTRACT

A protective oxygen mask is disclosed herein. The mask includes a main body defining an exterior surface and an interior portion. At least one attachment structure defines a first loop extending from a first side of the main body and a second loop extending from a second side of the main body. At least a portion of one of the loops includes a hollow tube section communicative with an oxygen source. An interior tube communicative with the hollow tube section of the first loop extends at least partially into the interior portion of the main body. Accordingly, oxygen flows from the oxygen source, through said hollow tube section of one of the loops, into the interior hollow tube section, and finally, into the interior portion of the main body via a plurality of openings.

17 Claims, 7 Drawing Sheets

OXYGEN MASK

FIELD OF THE INVENTION

The present invention is generally directed to a protective face mask, and more specifically, a face mask that is configured to deliver a flow of oxygen to an interior portion thereof through one or more of the attachment straps thereof.

BACKGROUND OF THE INVENTION

Protective face masks are known and are often worn by personnel in the medical field to prevent or restrict the transmission of respiratory droplets or other particles there through during a medical procedure or consultation. Recently, however, the use of protective face masks has extended to non-medical circumstances and everyday activities, particularly as a way to reduce the spread of the coronavirus or SARS-CoV-2 that causes COVID-19.

More in particular, in many locations in the United States and other countries worldwide, large gatherings of people are either prohibited or at least strongly discouraged. Furthermore, while some businesses are closed during the current COVID-19 pandemic, many are open but require patrons to wear a face mask at all times. Similarly, public transportation, such as that provided by buses, trains and particularly airplanes, are limited or at least reduced in number, although many if not all of those still in operation require all patrons to wear a face mask during the entire trip. This can be difficult for many individuals, particularly for those that travel long distances by airplane.

Furthermore, many people believe or are concerned that wearing a face mask for an extended period of time can be unhealthily or even dangerous due to the consistent inhaling or breathing in of large amounts of carbon dioxide. This may be especially true for those individuals who have been diagnosed with respiratory or other diseases or ailments.

Accordingly, there is a need in the art for a protective face mask that can deliver a flow of oxygen to the user wearing the mask from an oxygen source, such as a portable oxygen tank or vessel. The proposed mask can increase the oxygen concentration within the mask and reduce the amount of carbon dioxide inhaled while the mask is worn. It is contemplated that such a mask can solve many of the problems or concerns with regard to current face masks, and could potentially allow for the reopening of many establishments including large-crowd venues, such as stadiums, convention centers, theaters, schools, universities, etc.

SUMMARY OF THE INVENTION

Accordingly, the present invention is generally directed to an oxygen mask which can include a main body which may be in the form of or otherwise have a design similar in construction as a conventional N95 or KN95 mask or respirator, surgical mask, cloth mask, paper mask, or virtually any mask capable of being worn on a user's face and which at least partially peripherally covers the user's nose and mouth. In this manner, the main body of the various embodiments of the present invention can be constructed out of virtually any material that is capable of resisting the flow of particles, such as airborne particles, viruses, bacteria, etc. through the mask and into the interior portion thereof.

Furthermore, the mask of at least one embodiment of the present invention includes an attachment structure which secures the mask to the user and which is configured to deliver a flow of oxygen or other gas into the interior portion where it can be inhaled by the user. More specifically, at least one of the straps which can function to secure the mask to the user's face is constructed out of a flexible plastic tube, or otherwise includes one or more sections which is/are constructed out of a flexible plastic tube through which oxygen or other gas can flow from an oxygen or gas source. The oxygen or gas source can be virtually any portable or non-portable oxygen storage vessel, including, for example, a small portable oxygen tank or concentrator which can be easily carried around by the user, for example, in a backpack or other carrying bag or case.

A connecting tube attached to the gas source can be removably or fixedly connected to the attachment structure of the mask or one or more of the plastic tube straps, for example, by snapping or screwing the connecting tube thereto, allowing the user to use the mask for extended periods of time.

Moreover, the flow of oxygen from the source to the mask can be intermittent and/or regulated directly on the mask or tank, or in some embodiments, remotely via a remote device, such as a mobile phone, tablet, etc.

In some embodiments, one or more exit holes, openings or one-way exit valves, for example, in the main body and/or in the other or second strap/loop can be used to dispel carbon dioxide from the interior portion of the mask.

In this manner, the mask(s) of certain embodiments of the present invention can be worn by patrons participating in large gatherings, for example, but not limited to those at concerts, sporting events, conventions, movie theaters, theaters, operas, gyms, etc. in that the masks can be worn for long periods of time without the feeling of suffocation and the risk of breathing too much carbon dioxide. In addition, the masks and gas sources or tanks can be worn by school children in that the gas source may be small enough to be worn as or in a backpack or mounted to the back of students' chairs. In some cases, the tanks may be left at the school or on-site in any location, such that when the students or other individuals arrive at the location (e.g., at school, on a bus, train or airplane, in a theater, professional workspaces, offices, hospitals, clinics, etc.), the user can simply connect his or her mask to the gas source. This would also allow the individual(s) to remove the mask(s) from the gas source(s) upon departure such that the individual(s) can disconnect the gas source while keeping the mask on his or her face.

These and other objects, features and advantages of the present invention will become more apparent when the drawings as well as the detailed description are taken into consideration.

BRIEF DESCRIPTION OF THE DRAWINGS

Like reference numerals refer to like parts throughout the several views of the drawings provided herein.

DETAILED DESCRIPTION OF THE INVENTION

Figure 1:
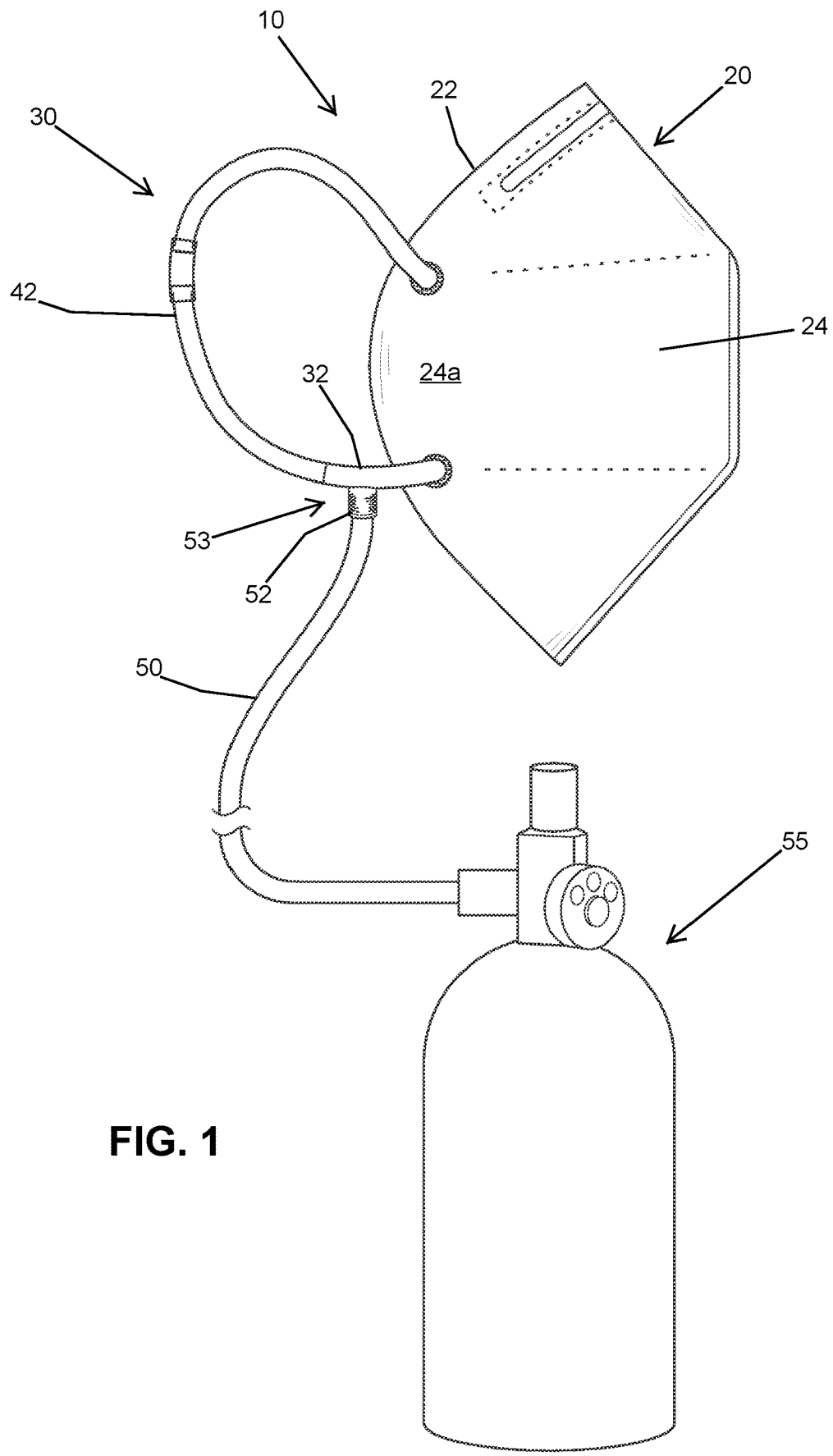
FIG. 1 is a side view of the oxygen mask and oxygen source as disclosed in accordance with at least one embodiment of the present invention.

As shown in the accompanying drawings, and with particular reference to FIG. 1, the present invention is directed to a protective mask, generally referenced as 10, which is structured and configured to deliver an amount of gas, including but not limited to oxygen and/or a blend of gases, to a user wearing the mask 10. For example, as described herein, the mask 10 of the various embodiments is connected to a gas or oxygen source 55 which provides a flow of gas or oxygen into the mask 10 through one or more tubes 50, 32, 34 and into the mask 10. In some embodiments, one or more of the straps which is/are used to attach or secure the mask 10 to the face of the user is/are constructed out of one or more hollow tubes through which the gas or oxygen may flow.

In particular, the mask 10 of the various embodiments of the present invention includes a main body 20 which may be in the form of or otherwise consistent with an N95 mask or respirator, a KN95 mask or respirator, a surgical mask, cloth mask, paper mask or virtually any mask capable of being worn on the user's face and which at least partially peripherally covers the user's nose and mouth. In this manner, the main body 20 of the various embodiments of the present invention can be constructed out of virtually any material that is capable of resisting the flow of particles, such as airborne particles, viruses, bacteria, etc. through the mask 10 and into the interior portion 25 thereof.

As an example, when worn, the protective face mask 10 of the various embodiments described herein, is intended to provide or act as a physical barrier covering the wearer's nose and mouth in a manner to block or substantially block the transmission of respiratory droplets or other particles from passing therethrough, and consequently, to help reduce the spread of airborne and other viruses (e.g., the coronavirus or SARS-CoV-2 that causes COVID-19), as well as other viruses, bacteria, infections, etc.

Accordingly, the mask 10, and in particular, the main body 20 thereof, may be constructed out of, but is not in any manner limited to, fabric, cloth, rubber, neoprene, polypropylene, polyisoprene, paper, etc. For instance, it is worth noting that N95 is a rating certification about performance of the mask in that an N95 rating requires masks to capture or block 95% of particles. Thus, an N95 mask can be constructed out of virtually any material, so long as it meets the N95 performance requirements. It should also be noted that the mask 10 of the present invention is not limited to N95 or KN95 compliant masks, and thus, the mask 10 provided herein may not meet the N95 or KN95 performance requirements but may still fall within the full spirit and scope of the present invention.

Figure 2:
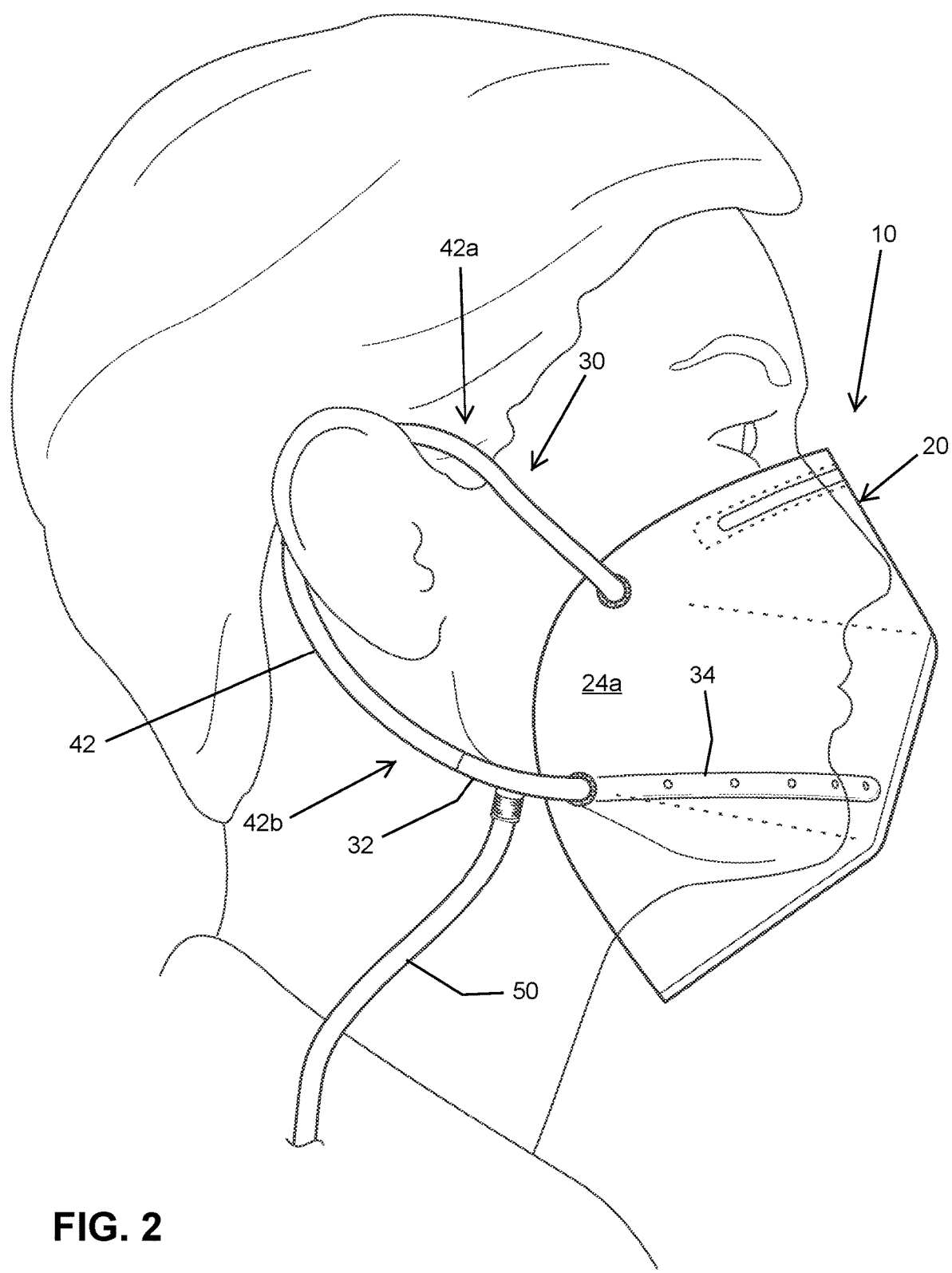
FIG. 2 is a side view of the oxygen mask being worn by a user in accordance with at least one embodiment of the present invention.

In any event, the main body 20 of the mask 10 of at least one embodiment includes a peripheral edge or boundary 22 which, as shown in FIG. 2, is sized to at least partially enclose a nose and mouth of the user. More specifically, a typical N95 mask is often designed to achieve a tight or close facial fit for efficient filtration of airborne particles forming a seal, or at least partially forming a seal around the nose and mouth. It should be noted, however, that other more loosely fitting masks, such as surgical masks, cloth masks, etc. which may not form a tight seal around the nose and mouth are still within the scope of the present invention and may still be sized to at least partially enclose a nose and mouth of the user. Thus, while some embodiments of the main body may form a seal around the nose and mouth of the user similar to an N95 mask, other embodiments may not.

Furthermore, the mask 10 of the present invention includes an attachment structure 30 or one or more straps or loops for facilitating attachment of the main body 20 to the face of the user. As described herein, in at least one embodiment, the attachment structure 30 may be entirely or substantially formed of one or more sections of a flexible and hollow tubular material, such as a plastic or other like tube. In other embodiments, however, it should be noted that the attachment structure 30 may be formed of various materials, such as one or more elastic or inelastic band sections combined with one or more hollow tube sections.

For example, in one implementation or embodiment, the attachment structure 30 forms two loops, such as a first loop 42 extending from one side 24*a* of the main body 20 and a second loop 44 extending from a second side 24*b* of the main body 20. In such an embodiment, the loops 42, 44 can wrap around or at least partially wrap around the rear portion the user's ears in order to position the main body 20 over the nose and mouth. Other embodiments, the attachment structure may form one or more head loops (not shown) extending from one side 24*a* of the main body 20 to the other side 24*b* of the main body 20. The one or more head loops may wrap around or at least partially around the rear portion of the user's head and/or neck area in order to secure the main body 20 to the face. Other attachment structures, straps, and configurations which facilitate attachment of the main body 20 to the face of the user are contemplated within the full spirit and scope of the present invention.

Moreover, the mask 10 of the various embodiments of the present invention includes at least one hollow tube or conduit, for example, defined by sections 32, 34, which is communicative with the interior portion 25 of the main body 20 of the mask 10. Specifically, as disclosed herein, the hollow tube(s) or hollow tube sections 32, 34, such as but not limited to an entry or external hollow tube section 32 and an internal hollow tube section 34, are interconnected to a gas source 55, such as a gas or oxygen tank, which is an oxygen storage vessel that can store and deliver oxygen or other gas(es). In some cases, the oxygen or other gas(es) are stored under pressure within the tank or vessel 55.

Furthermore, one or more openings 35 in one or more of the hollow tube(s) sections 32, 34 allow the oxygen or gas to be delivered into the interior portion 25 of the mask 10, allowing the user wearing the mask to then breathe the oxygen or gas. In other words, the hollow tube(s) or hollow tube section(s) 32, 34 of at least one embodiment include one or more openings or holes 35 communicative with the interior portion 25 of the main body 20 which expel, discharge, or otherwise deliver a flow of oxygen or gas. The flow of oxygen or gas can be a constant flow, an intermittent flow, and/or regulated or controlled via one or more valves or controls.

It should also be noted that the gas source 55 illustrated in FIG. 1 is exemplary in nature and should not be deemed limiting in any manner. More specifically, the gas source 55 can be virtually any gas source, and can be portable oxygen concentrators (POCs), or gas/oxygen cylinders of virtually any size, capacity or dimension whether portable or not portable. In this manner, the gas source of some embodiments may be sized such that it can be worn on the user's back or carried in a backpack, bag or other portable carrying device. Other embodiments may utilize larger gas cylinders than can be transported or moved on wheels, attached to a wheeled cart, etc. Still in other embodiments, a larger and substantially non-portable gas source may supply gas or oxygen to one or a plurality of masks 10, which may be useful in mass transit environments, such as on airplanes, trains or buses.

In any event, at least one embodiment of the present invention includes at least one connecting tube 50 which interconnects the mask 10, and in particular, the hollow tube(s) or hollow tube section(s) 32, 34 thereof, to the gas source 55. This allows the gas or oxygen to flow from the source 55, through the connecting tube 50, into the hollow tube(s) 32, 34, out of the one or more openings 35 and into the interior portion 25 of the main body 20 where it is available for the user wearing the mask 10 to breathe.

For instance, in at least one embodiment, the connecting tube 50 may be removably connected to the hollow tube(s) or hollow tube section(s) 32, 34 of the mask 10, which allows the user to selectively connect or disconnect the mask 10 from the gas source 55. In this manner, the mask 10 may be used or worn without being interconnected to the gas source 55, if desired, in which the mask 10 will function or operate much like a typical N95 mask, surgical mask, or other facial covering to prevent or restrict the flow of airborne particles into the mask 10. When or if desired, the user can interconnect the mask 10 to the gas source 55 by simply attaching the connecting tube 50 to a coupler, valve 52 or other like device located on the mask 10 and communicative with the hollow tube sections 32, 34 thereof. In some embodiments, the connecting tube 50 is screwed into the coupler or valve 52, although other manners in which to connect or attach the connecting tube 50 to the mask 10 are contemplated.

In some embodiments, the coupler or valve 52 disposed at the juncture 53 where the connecting tube 50 is interconnected to the hollow tube(s) 32, 34 of the mask 10 can be used to adjust or control the flow of oxygen or as into the hollow tube(s) 32, 34, and therefore, adjust or control the flow of oxygen or gas into the mask 10. Accordingly, the couple or valve 52 of certain embodiments may be rotated or twisted to adjust or control the size or diameter of a valve opening, which in turn adjusts or controls the flow of oxygen or gas therein. Of course, other valves and flow control mechanisms are contemplated within the full spirit and scope of the present invention.

Figure 3:
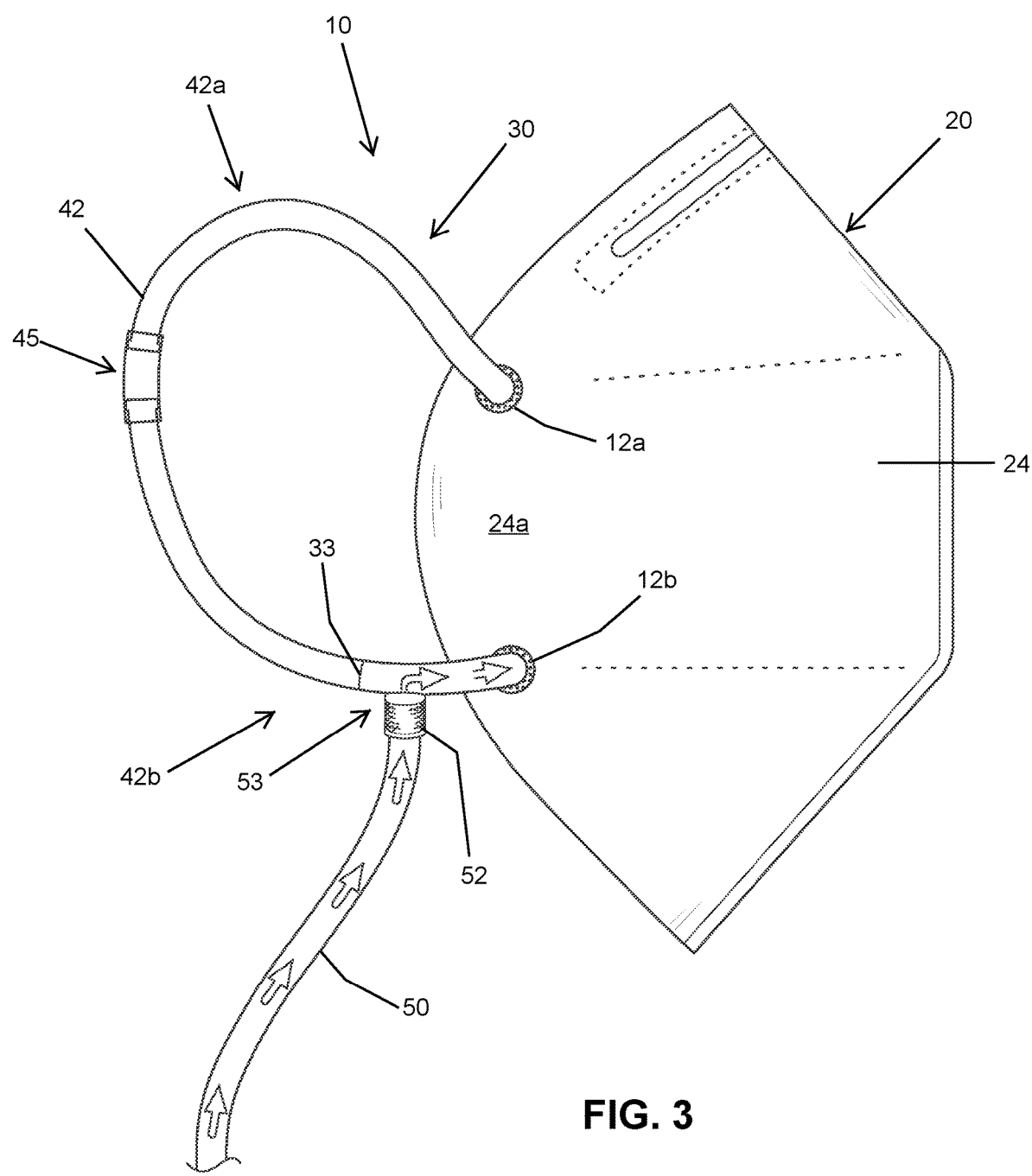
FIG. 3 is a side view of the oxygen mask illustrating a flow of oxygen through the connecting tube and hollow tube section of the first loop as disclosed in accordance with at least one embodiment of the present invention.

Turning now to FIG. 3, the first side 24a of the main body 20 and the first loop 42 of the attachment structure 30 is shown. In particular, the first loop 42 includes an upper portion 42a and a lower portion 42b extending from the first side 24a of the main body 20. In this embodiment, at least a section of the first loop 42, and in particular, at least a section of the lower portion 42b of the first loop 42 includes a hollow tube section 32 through which the oxygen or gas can flow, as illustrated by the series of arrows shown in FIG. 3. As illustrated, the hollow tube section 32, such as an entry or external hollow tube section 32, is disposed external to the main body 20 and is where the connecting tube 50 attaches.

In some embodiments, the entire first loop 42 or strap, including upper portion 42a and lower portion 42b, may be constructed out of a tubular material, while in other embodiments, one or more portions of the first loop 42 or strap (e.g., portions other than hollow tube 32) may be constructed out of other materials, including, but in no way limited to plastic, elastic, fabric, etc.

At least in the embodiment where the entire first loop 42, or a substantial portion of the first loop 42, is constructed out of a tubular material (and in other embodiments, as well), a flow blocker/restrictor 33 may be disposed along the loop 42 such that the connecting tube 50 connects to the hollow tube section 32 between the main body 20 and the flow blocker/restrictor 33. As shown in FIG. 3 the flow blocker or flow restrictor 33 is disposed adjacent or proximate the juncture 53 away from the main body 20; however, it is contemplated that the flow blocker or restrictor 33 can be disposed anywhere along the loop 42, such as within lower portion 42b or for example, between the upper portion 42a and the juncture 53. In any event, the flow blocker 33 is intended to block or restrict a flow of oxygen or gas from entering into the upper portion 42a of the loop 42 and instead direct the flow of oxygen or gas through the hollow tube section 32 and into the interior portion 25 of the main body 20.

Still referring to FIG. 3, in at least one embodiment, and adjustment coupler or adjustment structure, referenced as 45, maybe included along the length of the loop 42. More specifically, in one embodiment, upper portion 42a and lower portion 42b may be constructed out of a plastic (or other) tubular material. Upper portion 42a and lower portion 42b may, in some cases, be interconnected to one another via a coupler or adjustment structure 45, which can allow the size of the loop to be adjusted so that the loop can comfortably fit users of various sizes. As just an example, the adjustment structure 45 of at least one embodiment may include a coupler defining opposing ends which can adjustably connect to corresponding ends of the upper and lower portions 42a, 42b of the loop 42, as shown in FIG. 3, for example. The upper and/or lower portions 42a, 42ab can slide or be pushed further into (or in a different embodiment, onto) the coupler 45 in order to shorten the loop 42. Conversely, pulling the ends of the upper and lower portions 42a, 42b away from each other, while still being connected to the coupler 45 will serve to lengthen the loop 42. It should be noted that other adjustment couplers and structures are contemplated and which allow for the selective adjustment of (e.g., lengthening and shortening) of the loop 42, as desired. It should also be noted that, although not shown in the figures, the second loop 44 may include a similar adjustment coupler or structure such that the second loop 44 can be adjusted in the same or similar manner.

Figure 4:
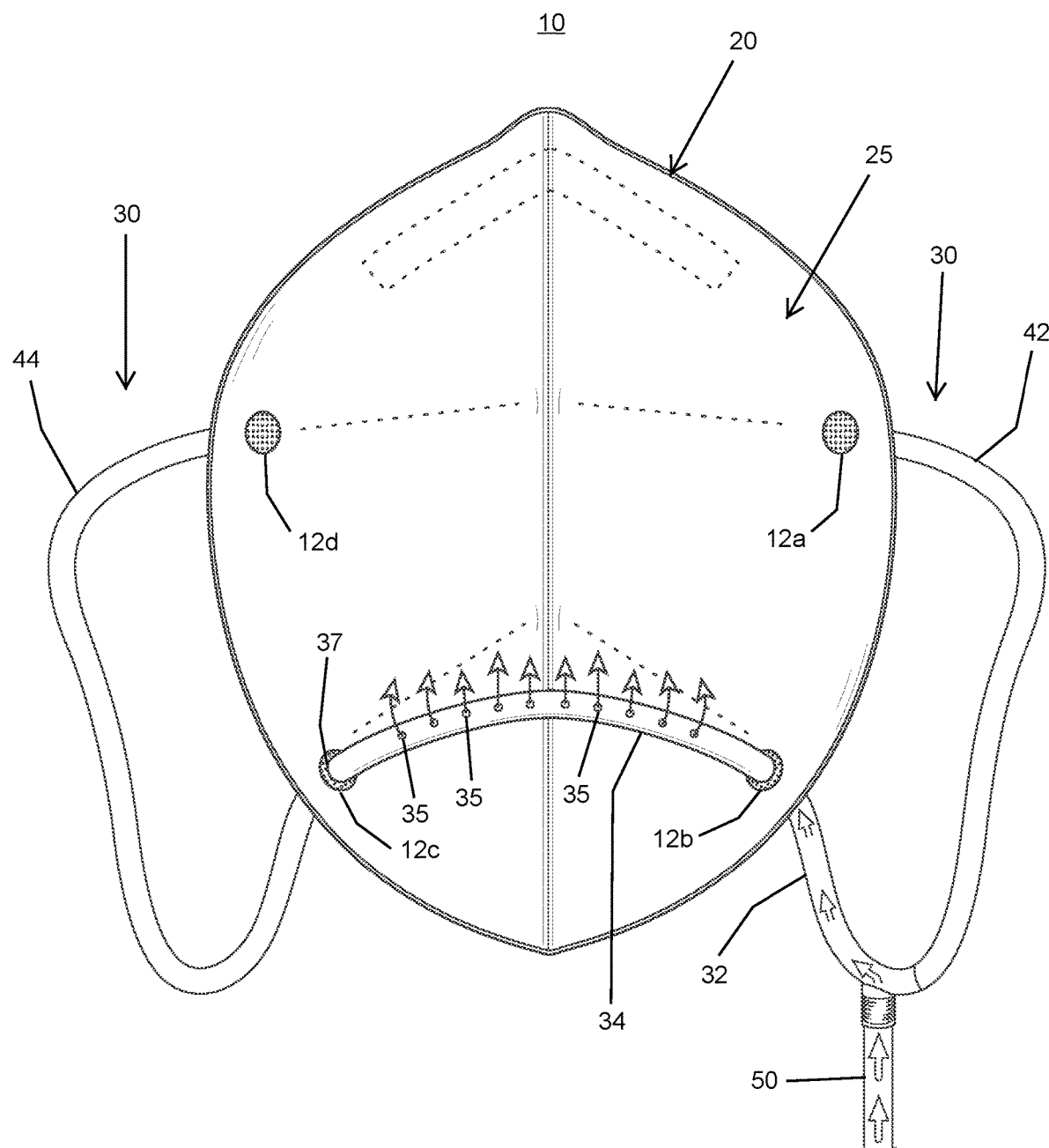
FIG. 4 is a rear and internal view of the oxygen mask as disclosed in accordance with at least one embodiment of the present invention.
Figure 5:
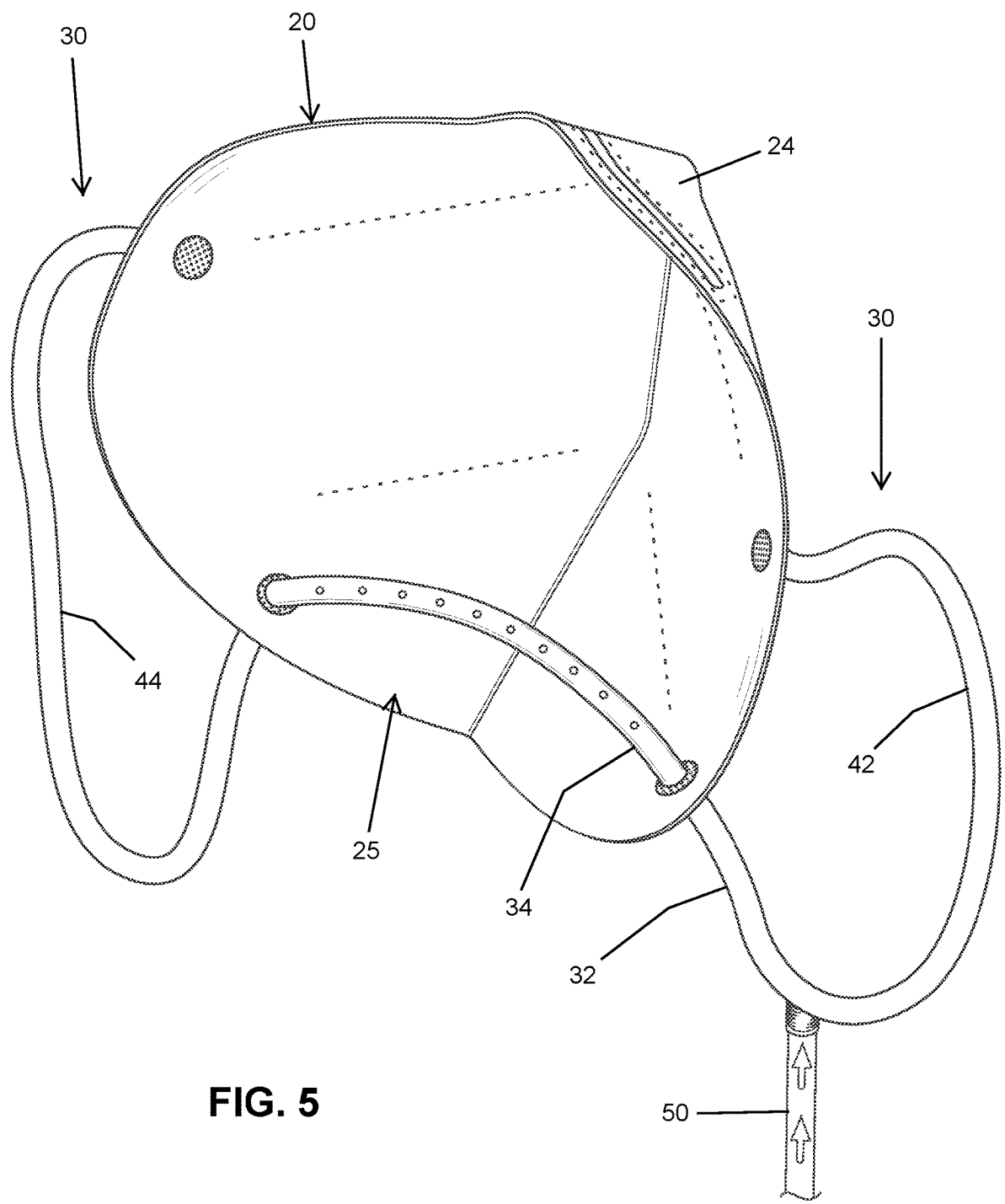
FIG. 5 is a perspective internal view of the oxygen mask as disclosed in accordance with at least one embodiment of the present invention.

Referring now to FIGS. 4 and 5, the hollow tube(s) of at least one embodiment also include an interior tube or an interior tube section 34 extending into the interior portion 25 of the main body 20. The interior tube section 34 is communicative with the exterior tube section 32 and, in at least one embodiment, includes at least one, or as shown in FIGS. 4 and 5, a plurality of openings or holes 35 disposed in a spaced relation to one another along a length of the tube 34. In this manner, as the gas or oxygen flows through the interior tube or section 34, the gas or oxygen will dispense or exit the tube 34 through the one or more openings 35 and enter the interior portion 25 of the main body 25 where the user wearing mask 10 can inhale the gas or oxygen.

Furthermore, the interior tube or section 34 may extend at least partially across the interior portion 25 of the main body 20, for example, from the first side 24a toward, and in some cases all the way to, the second side 24b. As shown, the interior tube or section 34 is positioned along the lower or bottom portion of the main body 20 (e.g., the lower half of the main body 20) such that the openings or holes 35 are proximate to the user's mouth and/or nose allowing for the gas or oxygen to be easily inhaled.

It should also be noted that in some embodiments, the attachment structure 40 which forms the first loop 42, exterior hollow tube 32 and interior hollow tube 34, is constructed of a single piece of hollow tube. In other words, the first loop 42 of at least one embodiment is attached to or at least extends from an exterior surface 24 of the main body at a first point 12a. First point 12a, in at least one embodiment is disposed on an upper section of first side 24a. The first loop 42 continues to the lower portion 42b where the exterior hollow tube section 32 is formed. As mentioned herein, in at least one embodiment, a stopper or flow restrictor 33 is disposed within the first loop 42 which defines the start of the exterior hollow tube section 32. The exterior hollow tube section 32 of at least one embodiment may extend into the main body 20 at a second point or location 12b, where the start of the interior tube section 34 is defined or formed.

Furthermore, in at least one embodiment, the interior tube section 34 may pass through the lower portion of the second side of the main body 20 at a third point or location 12c, where it begins to form the second loop 44. The hollow tube or strap will then attach or otherwise extend from a fourth point or location 12d on the exterior of the main body 20.

In addition, a further or additional stopper or flow restrictor may be disposed within the tube at or near the third point 12c such that the flow or air or oxygen will not extend through point 12c but is rather restricted to flowing through the exterior and interior hollow tubes 32, 34.

In this manner, the first loop 42, second loop 44 and interior hollow tube 34 may be constructed of a single piece of hollow tube with a connection at juncture 53 where connecting tube 50 is attached and with flow restrictors 33, 37 restricting the flow of oxygen to exterior hollow tube section 32 (disposed substantially between the juncture 53 and the main body 20) and/or interior hollow tube section 34 (disposed within the interior portion 25 of the main body 20.). Moreover, the flow restrictor(s) or blocker(s) 33, 37 may include a sphere, ball, disc, or other structure or device that is configured and structured to block or at least restrict the flow of gas or oxygen thereby. In some embodiments, for example, which include a separate adjustment coupler 45, the loops 42, 44 may be constructed out of separate pieces (e.g., upper portion and lower portion) adjustably connected to one another via the coupler 45.

Figure 6A:
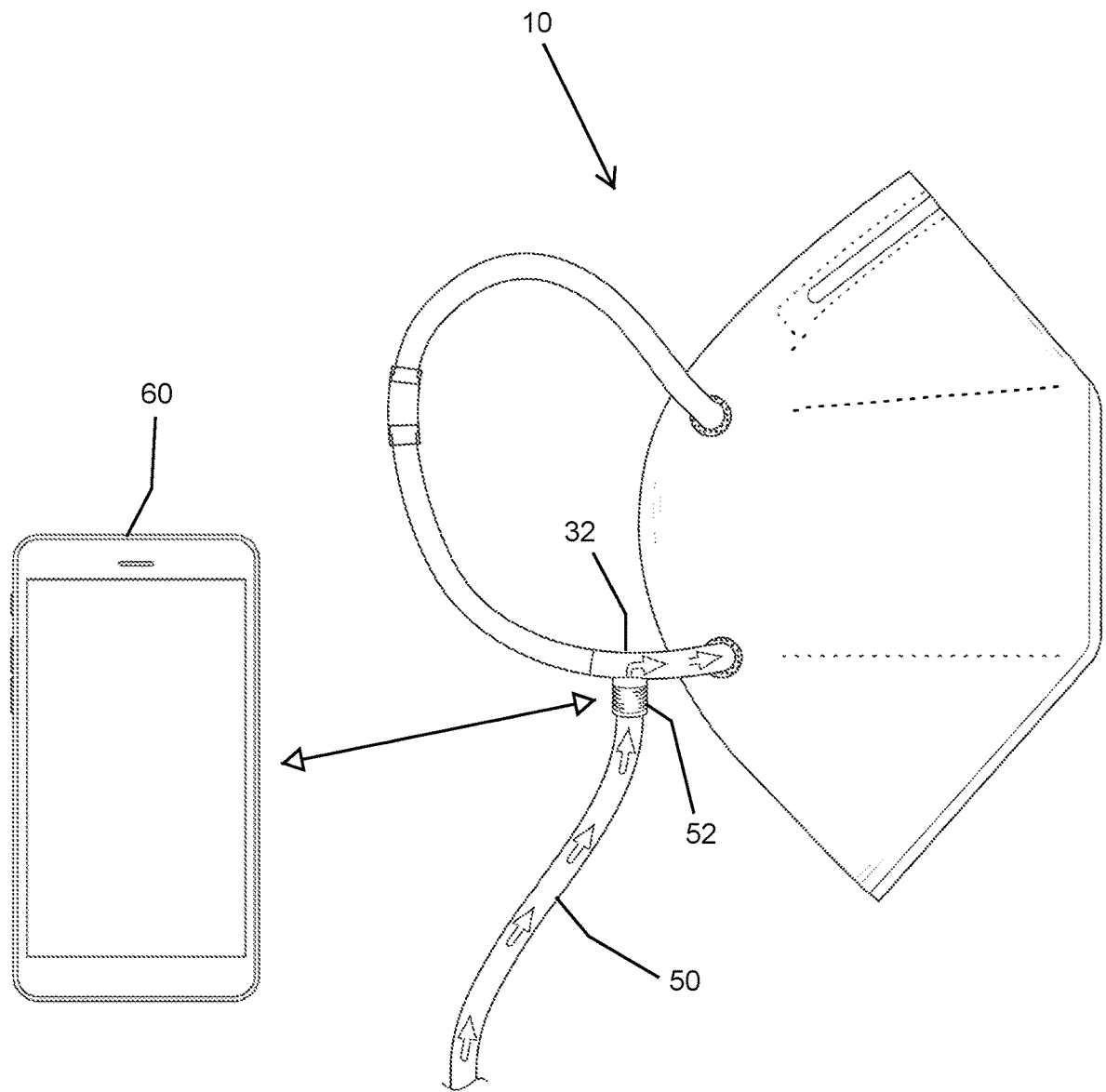
FIG. 6A is another side vice of the oxygen mask illustrating a remote communication with a mobile device as disclosed in accordance with at least one embodiment of the present invention.
Figure 6B:
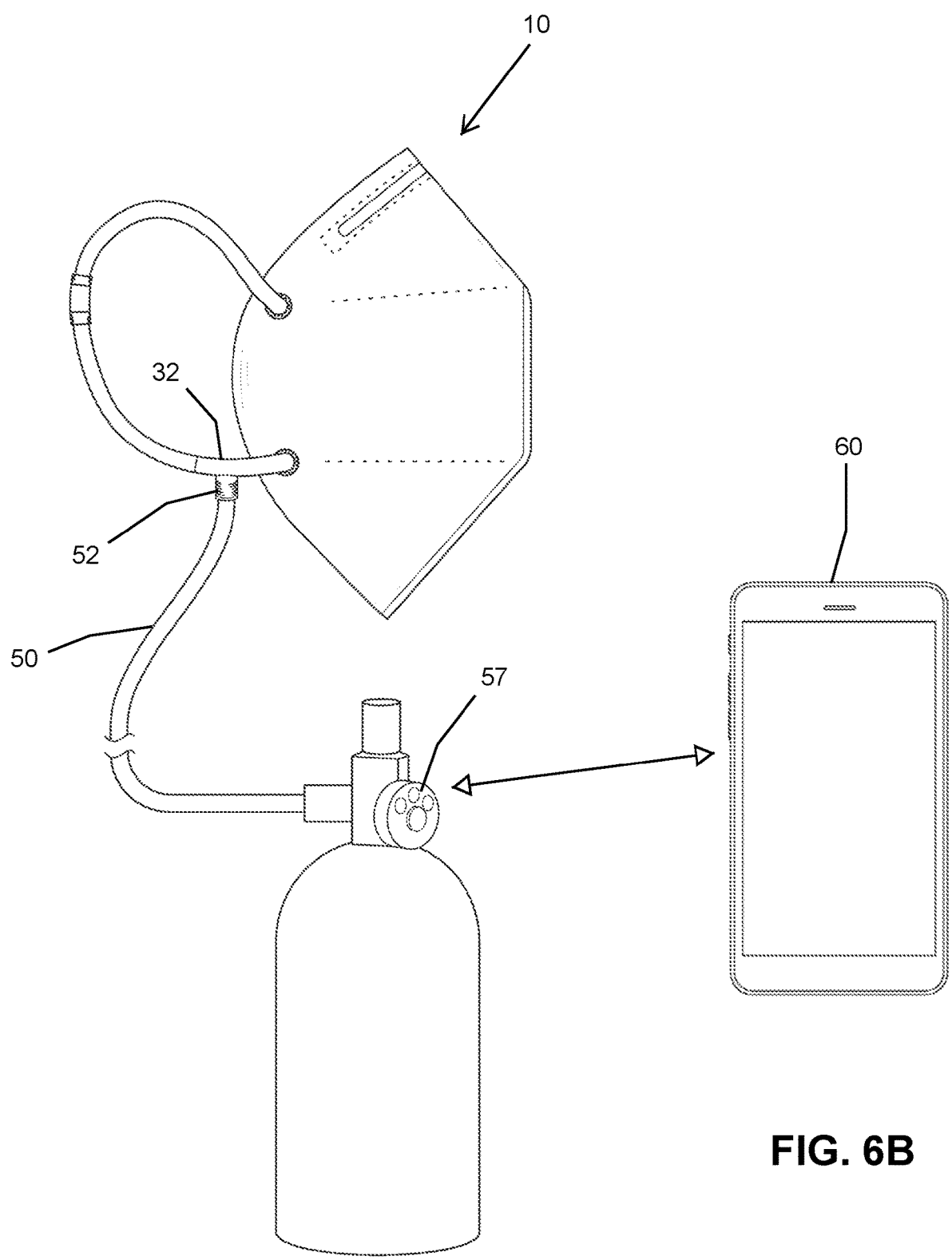
FIG. 6B is a side view of the oxygen mask and oxygen source illustrating another remote communication with a mobile device as disclosed in accordance with at least one embodiment of the present invention.

In other embodiments, it is contemplated that the attachment structure 40 is constructed of a plurality of separate pieces, tubes, straps, sections, etc. interconnected to one another to form the first loop 42, interior tube or section 34, and second loop 44. For example, the interior tube or section 34 may be connected, either removably or fixedly, to points or locations 12b and 12c so long as the interior tube or section 34 is communicative with the flow of air or oxygen from the connecting tube 50, such as, for example, via external tube 32. Furthermore, the first loop 42, or a portion of the first loop, such as the portion formed by the external hollow tube 32 of at least one embodiment, may be connected, either removably or fixedly, to the main body 20, for example, at point or location 12b, so long as the oxygen or gas flows to and through the interior tube or section 34. For instance, a tube connector Referring now to FIGS. 6A and 6B, yet another embodiment of the present invention is structured to allow the flow of oxygen or gas to be controlled or regulated through a remotely communicative device, including, but in no way limited to an off-the-shelf device, such as a mobile phone (e.g., APPLE® iPHONE®, ANDROID® phone, etc.) a tablet computer (e.g., APPLE® iPAD®, SAMSUNG® GALAXY® tablet, MICROSOFT® SURFACE® tablet, etc.), a laptop computer, desktop computer, game console, etc. In some embodiments, a designated or dedicated controller may be provided which mainly functions to communicate the one or more control valves or other devices, although other peripheral functionality may also be included. As shown in FIGS. 6A and 6B, the remote device 60 is representative of a mobile phone as just an example although it is not limited to such.

In any event, as shown in FIG. 6A, the remote device may be remotely communicative with valve 52 allowing the user to control or adjust the flow of gas or oxygen into the mask 10 via the remote device 60. In the embodiment of FIG. 6B, the remote device may be remotely communicative with a valve or other control mechanism 57 located on or connected to the gas source 50.

In such a manner, in the case of a mobile phone, tablet, computer, or other off-the-shelf device, the device 60 may be equipped with a designated mobile (or other) application which may be downloaded and installed on the device 60. The application can be stored on a storage medium (e.g., hard drive, solid state drive, etc. on the device or on a remote cloud-based drive) and can be executed by the device's hardware components, such as the device's processor(s), memory, etc. When the application is executed, it may be communicative with the one or more valves or control mechanisms 52, 57 such that when a user manipulates a setting, slider, dial or other feature on the device 60, the device 60 will communicate the valve setting to the valve(s) 52, 57 to adjust or control the flow of gas or oxygen to the mask. It should also be noted that, in some embodiments, and particularly but not limited to the embodiment where the remote device 60 is a designated device for controlling the flow of gas or oxygen, the setting, dial, slider or other feature may be implemented via a physical control mechanism, rather than or in addition to a software implementation in a mobile application.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. This written description provides an illustrative explanation and/or account of the present invention. It may be possible to deliver equivalent benefits using variations of the specific embodiments, without departing from the inventive concept. This description and these drawings, therefore, are to be regarded as illustrative and not restrictive.

Now that the invention has been described,

What is claimed is:

1. A protective mask for delivering a gas to a user, comprising:
   a main body comprising a peripheral boundary sized to enclose a nose and mouth of the user, said main body defining an exterior surface and an interior portion,
   at least one attachment structure for facilitating attachment of said main body to a face of the user, wherein at least a portion of said at least one attachment structure comprises at least one hollow tube section, said at least one hollow tube section comprising at least one opening communicative with said interior portion of said main body, at least one connector tube interconnecting said at least one hollow tube section of said at least one attachment structure to a gas source, wherein said at least one connector tube is removably connected to said at least one hollow tube section of said at least one attachment structure, an adjustable valve for controlling a flow of gas into said interior portion of said main body, wherein said adjustable valve is disposed at a juncture where said at least one connector tube is connected to said at least one hollow tube section, and wherein the gas flows from said gas source, through said at least one connector tube and said at least one hollow tube section and out of said at least one opening into said interior portion of said main body.

2. The protective mask as recited in claim 1 wherein said at least one attachment structure defines a first loop extending from a first side of said main body and a second loop extending from a second side of said main body.

3. The protective mask as recited in claim 2 wherein said first loop comprises an upper portion and a lower portion both extending from said first side of said main body.

4. The protective mask as recited in claim 3 wherein said at least one hollow tube section comprises an exterior hollow tube section disposed on said lower portion of said first loop.

5. The protective mask as recited in claim 4 wherein said at least one hollow tube section further comprises an interior tube section extending at least partially across said interior portion of said main body, said interior tube section being communicative with said exterior tube section.

6. The protective mask as recited in claim 5 wherein said at least one opening is disposed along a length of said interior tube section.

7. The protective mask as recited in claim 6 wherein said interior tube section comprises a plurality of openings disposed along said length thereof.

8. The protective mask as recited in claim 6 wherein said interior tube section extends between a lower portion of said first loop to a lower portion of said second loop.

9. The protective mask as recited in claim 8 further comprising a flow blocker disposed between said upper portion of said first loop and said at least one connector tube to restrict a flow of gas into said upper portion of said first loop.

10. The protective mask as recited in claim 9 further comprising another flow blocker disposed within said continuous hollow tube to restrict a flow of gas into said second loop.

11. A protective oxygen mask, comprising:
a main body defining an exterior surface and an interior portion,
at least one attachment structure defining a first loop extending from a first side of said main body and a second loop extending from a second side of said main body,
wherein said first loop comprises a continuous hollow tube defining an upper loop portion and a lower loop portion,
wherein at least a portion of said first loop comprises an exterior hollow tube section,
an interior hollow tube section extending from and communicative with said exterior hollow tube section of said first loop, sand interior tube section being disposed within said interior portion of said main body, and
at least one connector tube interconnecting said exterior hollow tube section of said first loop to an oxygen source, wherein the oxygen flows from the oxygen source, through said at least one connector tube, through said hollow tube and out of said at least one opening into said interior portion of said main body.

12. The protective oxygen mask as recited in claim 11 wherein said exterior hollow tube section of said first loop and said interior hollow tube section comprise a unitary construction.

13. The protective oxygen mask as recited in claim 11 wherein said exterior hollow tube section of said first loop and said interior hollow tube section are connected to one another.

14. The protective oxygen mask as recited in claim 11 further comprising a flow blocker disposed within said first loop and configured to restrict a flow of oxygen into said upper portion of said first loop.

15. A protective mask for delivering a gas to a user, comprising:
a main body comprising a peripheral boundary sized to enclose a nose and mouth of the user, said main body defining an exterior surface and an interior portion,
at least one attachment structure for facilitating attachment of said main body to a face of the user, wherein at least a portion of said at least one attachment structure comprises at least one hollow tube section, said at least one hollow tube section comprising at least one opening communicative with said interior portion of said main body,
wherein said at least one attachment structure defines a first loop extending from a first side of said main body and a second loop extending from a second side of said main body,
wherein said first loop comprises an upper portion and a lower portion both extending from said first side of said main body,
wherein said at least one hollow tube section comprises an exterior hollow tube section disposed on said lower portion of said first loop,
wherein said at least one hollow tube section further comprises an interior tube section extending at least partially across said interior portion of said main body, said interior tube section being communication with said exterior hollow tube section,
wherein said at least one opening is disposed along a length of said interior tube section,
wherein said interior tube section extends between a lower portion of said first loop to a lower portion of said second loop, and
at least one connector tube interconnecting said at least one hollow tube section of said at least one attachment structure to a gas source,
wherein the gas flows from said gas source, through said at least one connector tube and said at least one hollow tube section and out of said at least one opening into said interior portion of said main body.

16. The protective mask as recited in claim 15 further comprising a flow blocker disposed between said upper portion of said first loop and said at least one connector tube to restrict a flow of gas into said upper portion of said first loop.

17. The protective mask as recited in claim 16 further comprising another flow blocker disposed within said continuous hollow tube to restrict a flow of gas into said second loop.

* * * * *